United States Patent [19]

Guesdon et al.

[11] Patent Number: 4,900,661
[45] Date of Patent: Feb. 13, 1990

[54] METHOD FOR IMMUNOLOGICAL DETERMINATION OF AMINES, MONOCLONAL ANTIBODIES AND KIT OF REAGENTS FOR CARRYING OUT THE METHOD

[75] Inventors: Jean-Luc Guesdon; Stratis Avrameas; Jean-Claude Mazie, all of Paris, France

[73] Assignees: Institut Pasteur; Centre National de la Recherche Scientifique (CNRS), both of Paris, France

[21] Appl. No.: 828,854

[22] Filed: Feb. 12, 1986

[30] Foreign Application Priority Data

Feb. 14, 1985 [FR] France ................................ 85-02130

[51] Int. Cl.[4] .................. G01N 33/53; G01N 33/566; C12N 15/00
[52] U.S. Cl. ..................................... 435/7; 435/172.2; 435/810; 436/501; 436/548; 436/808; 530/387; 935/89; 935/95
[58] Field of Search .................... 435/7, 133; 436/548, 436/528, 501

[56] References Cited

U.S. PATENT DOCUMENTS 4,481,298 11/1984 Cone, Jr. et al. .................. 436/500

*Primary Examiner*—Robert J. Warden
*Assistant Examiner*—Janelle Graeter
*Attorney, Agent, or Firm*—Bierman and Muserlian

[57] ABSTRACT

This method for immunological determination of amines in biological media consists of: (a) reacting a quinone (in particular, p-benzoquinone) with the amine (for example histamine) present in the test sample; (b) introducing into the medium a monoclonal antibody which specifically recognizes the amine-quinone reaction product formed; and (c) determining one of the forms of the monoclonal antibody present. When the quinone is used in the immobilized state, the monoclonal antibody present is determined in its complexed form with the amine-quinone reaction product (direct type method); when the quinone is used in the free state, the monoclonal antibody is determined in its free form (enzymoimmunometric method or competitive immunoenzymatic method).

24 Claims, 4 Drawing Sheets

METHOD FOR IMMUNOLOGICAL DETERMINATION OF AMINES, MONOCLONAL ANTIBODIES AND KIT OF REAGENTS FOR CARRYING OUT THE METHOD

The present invention relates to a method for the immunological determination of amines present in biological media, the monoclonal antibodies specific for the products resulting from the reaction of the amine with a quinone, the hybridomas secreting these antibodies and the kits containing the reagents required for carrying out the method of determination.

The determination of histamine is one of the most significant tests for immediate hypersensitivity. Several methods for the determination of histamine are currently available, but these methods can only be carried out in laboratories which possess expensive apparatus.

The method most commonly used clinically is based on a fluorimetric determination involving the extraction of the serum to be studied with butanol, followed by treatment with an aqueous solution of hydrochloric acid containing heptane. The histamine extracted into the hydrochloric acid phase is condensed with o-phthalaldehyde, an alkaline medium, to form a fluorescent compound; the fluorescence measured is proportional to the amount of histamine present in the medium, the histamine having liberated by the basophils or the mast cells. This technique is tedious and awkward, even when automated.

The radio-enzymatic method, also employed, presents problems of specificity; as, for example, chlorpromazine and serotonin inhibit the enzyme activity of histamine N-methyltransferase.

Another method uses gas phase chromatography coupled to mass spectrometry, and consequently involves the use to complex and especially expensive apparatuses.

It would thus be especially advantageous to be able to determine histamine by an immunological method, since these disadvantages would be avoided. In effect, since such a method is specific, it would not be necessary to carry out chemical extraction of the histamine, and furthermore the method would be sensitive, since methods are known for labeling antibodies with substances which can be readily determined even in very small amounts, for example with enzymes, radioisotopes and fluorochromes.

Unfortunately, it appeared to be particularly difficult to obtain specific antibodies to histamine, and as H. Mita et al recently stated, in Agents and Actions 14 p. 574–579 (1984), they had been unable to obtain antibodies directed against histamine or against histamine/bovine serum albumin conjugates in rabbits.

It has now been found that, by conjugating histamine to a compound of low molecular mass, a quinone, it is possible to obtain antibodies specific for the histamine/quinone addition compound which could be used in a method for the immunological determination of histamine.

In that which follows, reference will be made to histamine, but it will be clear to the expert that the method for obtaining antibodies and the use of the latter is also applicable to other amines present in biological media and capable of forming addition compounds with a quinone, that is to say primary or secondary amines.

Among the latter, neurotransmitters such as dopamine or norepinephrine, amino acids such as glycine or glutamate, and pentides of low mass such as enkephalin, substance P or neurotensin may be mentioned.

In the method for the immunological determination of amines in biological media, which forms the subject of the present invention:

(a) the amine present in the sample to be studied is reacted with a quinone;
(b) a monoclonal antibody which specifically recognizes the amine-quinone reaction product formed is then introduced into the medium; and
(c) determination is carried out of one of the forms of the monoclonal antibody present, either free or immobilized form.

The quinones which can be suitable include naphthoquinone, pyrenequinone, perylenequinone, diphenoquinone and benzoquinones. p-Benzoquinone which, like $\alpha,\beta$-ethylenic ketones, can form 1,4-addition products is most especially preferred.

By monoclonal antibody specific for the amine-quinone reaction product, it is understood an antibody which complexes this quinone/amine product, in its free or immobilized form, without complexing either the amine alone or the quinone, whether the latter be free or immobilized as will be described below, this antibody also not binding, in the case of an immobilized quinone, to the substance used for coupling the said quinone to its insoluble support, nor binding to the said support, as will be described below.

It is especially surprising that it is possible to obtain such monoclonal antibodies which recognize the product resulting from the reaction of the quinone with an amine without recognizing either of these separate structures.

These monoclonal antibodies are secreted by hybridomas prepared according to the known technique described for the first time by Köhler and Milstein in Nature, 256, 495–97 (1975). To obtain the cells which will be fused with mouse myeloma cells, mice are injected with a conjugate of the protein/amine to be studied, prepared by reacting the quinone in question with a protein and a polyamine used to couple the amine-quinone conjugate to the support, and then the primary amine with the "sensitized" protein thereby being obtained. The coupling of different compounds of high molecular mass to proteins via a quinone is described in various articles by S. AVRAMEAS and T. TERNYNCK including, in particular, Immunochemistry vol 14 p. 767 (1977); the same method is applied in this case.

The protein used for preparing the immunogenic conjugate can be, for example, bovine albumin, ovalbumin, an enzyme such as glucose oxidase or ribonuclease, or lamprey hemocyanin.

The hybridomas obtained by fusion of mouse myeloma cells, such as SP-2/0 or Ag 8×63-653, with spleen cells from immunized mice are selected by cloning and subcloning in such a way as to isolate the hybridoma lines which secrete monoclonal antibodies having a strong affinity for the 1,4-addition compound of the type of those of formula I or II shown below, and a negligible affinity for the free amine and the free or immobilized quinone, and also for the polyamine used for coupling the quinone to the insoluble support.

The immunoreactivity of the culture supernatants is monitored by a direct immunoenzyme technique. First, each supernatant is tested simultaneously in respect of the histamine-quinone-polyamine conjugate and the histidine-quinone-polyamine conjugate. The presence of antibodies bound to these two conjugates is revealed by means of enzyme-labeled anti-mouse IgG antibodies. Only the hybridomas which secrete antibodies which combine exclusively with the first conjugate are retained. The fine specificity of these antibodies is then analyzed by an inhibition technique, using quinone, the histamine-quinone compound, the histidine-quinone compound, the glycine-quinone compound, the polyamine, histidine, histamine and the histamine-quinone-polyamine, histidine-quinone-polyamine and glycine-quinone-polyamine conjugates as inhibitors. The hybridomas selected are those which secrete antibodies which exclusively recognize the histamine-quinone compound. By histamine-quinone (or histidine, or glycine) compound, it is understood the compound results from that this reaction of histamine (or histidine or glycine) with the quinone. The histamine-quinone-polyamine conjugate, is understood to be the result of the reaction of the quinone with the polyamine, followed by the reaction of the product obtained with histamine.

In the case of testing for monoclonal antibodies directed against an amine other than histamine, amines other than histidine or glycine, that is to say other structural analogs of the amine in question, may be used for the selection.

The hybridomas which secrete monoclonal antibodies having the affinity characteristics defined above, as well as these monoclonal antibodies, are another subject of the invention.

Samples of the preferred hybridoma prepared to date have been filed with the Collection Nationale de Microorganismes (National Microorganism Collection) at the Institut Pasteur, Paris, on 4th Feb. 1985, under the no. I 421.

According to the present invention, between stage (a) and stage (b) of the method described above, blocking of the remaining reactive groups of the quinone is performed in particular. This blocking is accomplished by reacting the compound resulting from the reaction of the quinone and the amine with an excess of a primary amine such as glycine, lysine, ethanolamine, tris(hydroxymethyl)aminomethane, known as TRIS, or the like.

According to a first embodiment of the method according to the present invention, in the stage (a), the quinone is used in the immobilized state on an insoluble support, the immobilization being achieved by the use of a polymer having an amine group, and in stage (c) determination is carried out by the monoclonal antibody present in the form of its complex with the amine-quinone reaction product.

By immobilized quinone, it is understood that the immobilized quinone is the quinone which has reacted with a polyamine—such as a protein, a polypeptide or a polyethyleneimine—which has been bound beforehand to an insoluble support—such as a microtitration plate, the walls of tubes or beads made of polystyrene, polypropylene, polyvinyl chloride, polyacrylamide and the like, or polyacrylamide, agarose or polyacrylamide/agarose gels. In the case of p-benzoquinone, the reaction scheme is as follows:

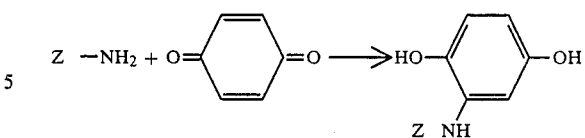

in which Z denotes the primary polyamine—only one amine group of which is shown—bound to a support. When the amine to be determined reacts with quinone, a 1,4-addition compound is obtained; in the case of free p-benzoquinone and a primary amine, represented by RNH$_2$, the reaction scheme is as follows:

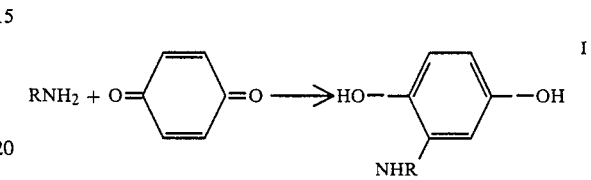

while when RNH$_2$ reacts with immobilized p-benzoquinone, the addition product is represented by the following formula:

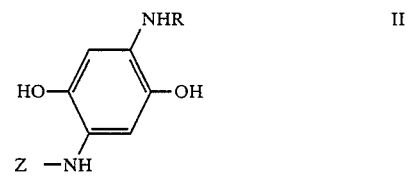

In the case of the abovementioned first embodiment of the method according to the invention, in the stage (c) an especially sensitive technique consists of reacting the monoclonal antibody, present in its complexed form, with an antibody directed against it and labeled with a component which can be measured and, after the reaction, determining the amount of the said labeled antibody which has bound to the said monoclonal antibody.

Among the agents known for labeling antibodies, radioactive elements, fluorescent components, enzymes and red cells may be mentioned. Enzymes, such as galactosidase, peroxidase, glucose oxidase and alkaline phosphatase, are preferred. This technique may be described as direct immunological determination.

According to a second embodiment of the method according to the present invention, in stage (a), the quinone is used in the free state, and in stage (c), the monoclonal antibody is determined in its free state.

In this case, it is possible, in particular, to proceed in two different ways to carry out stage (c):

in a first variant, in this stage (c), a known amount of compound resulting from the reaction of the amine in question with the quinone in question, the latter being immobilized on an insoluble support via a polymer having amine groups, is introduced into the medium, together with an antibody directed against the monoclonal antibody and labeled with a measurable component, and, after the reaction, determination is carried out of the amount of labeled antibody which has bound to the said support bearing the quinone-amine reaction product.

In a second variant, in this stage (c), the monoclonal antibody is preferably immobilized on a support, an enzyme-amine conjugate is added to the medium and the enzyme activity is determined, either on the support or in the liquid phase. A peroxidase is preferably used as the enzyme.

The samples in which the amines will be determined by the method of the invention can be prepared from biological fluids and tissues in a manner known per se, and diluted if necessary such that the concentration of the amines is generally between 10 pg/ml and 20 ng/ml; this concentration depends on the pH of the reaction medium, the affinity of the immunogenic agents present, the amount of quinone bound to the support and the nature of the labeling of the antibody used for visualization.

However, the implementation of stage (c) according to the second variant, using an "amine-enzyme" conjugate in which the amine/enzyme coupling involves the preservation of the enzyme activity, enables histamine, in particular, to be determined simply and reproducibly when the latter is present in a complex biological medium (for example, in whole blood).

Figure 1:
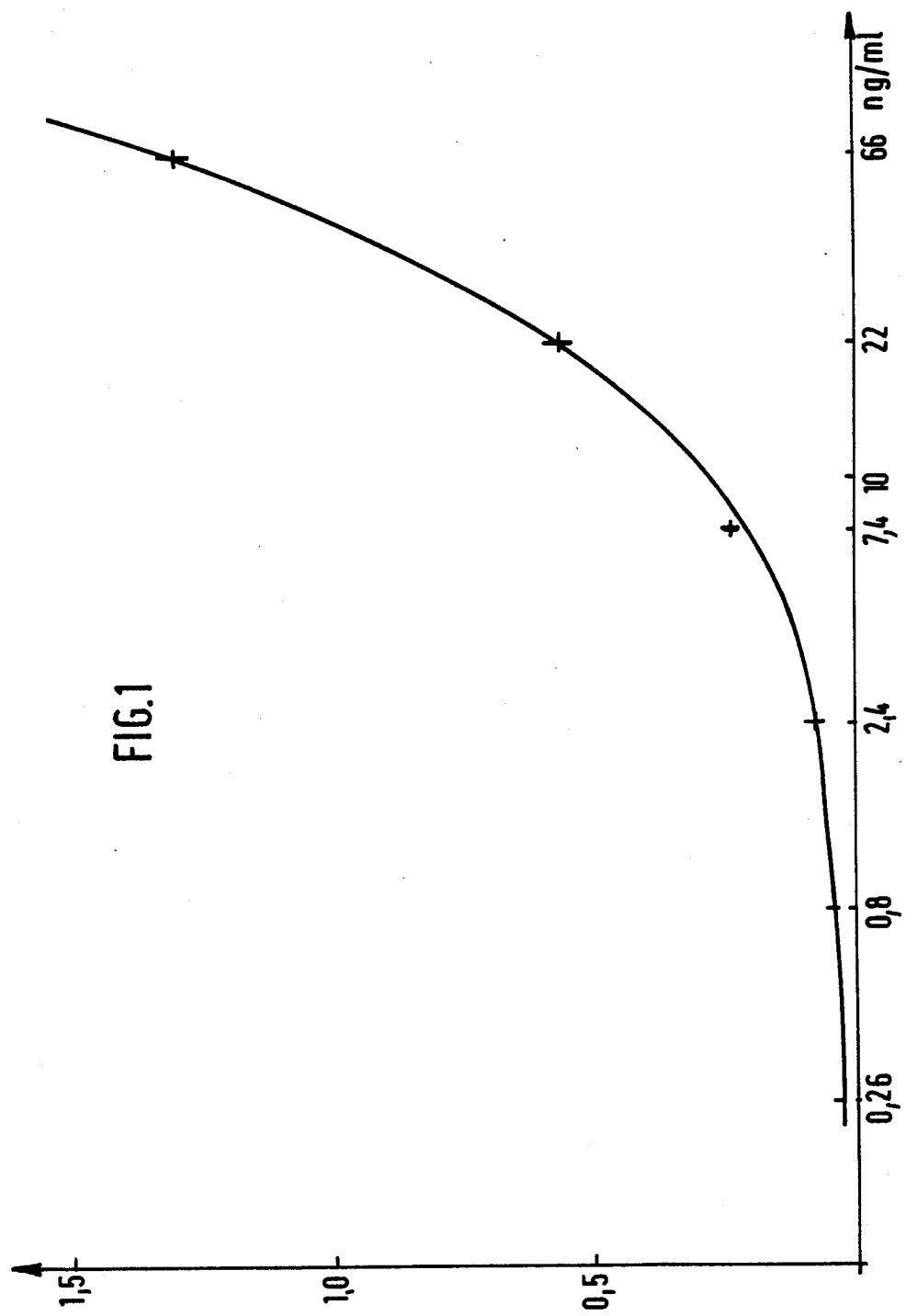
FIG. 1 shows, in semi-logarithmic co-ordinates, optical density at 414 nm read in terms of histamine concentration.

In that which follows, examples of implementation of the invention are described:

EXAMPLE 1

Production of hybridomas secreting monoclonal antibodies specific for the 1,4-addition compound formed by the action of para-benzoquinone on histamine (1) Preparation of the immunogen 10 mg of bovine albumin are dissolved in 2 ml of phosphate buffer (0.1M; pH 6.0) and 30 mg of p-benzoquinone, dissolved in 0.6 ml of ethanol, are added. After one hour of stirring at room temperature, the solution is chromatographed on a Trisacryl GF05 column, marketed by IBF-Pharmindustrie, which is based on acrylic copolymers; the column containing approximately 50 ml of gel having been equilibrated beforehand with 0.15M aqueous sodium chloride solution. The first fraction, up to a volume corresponding to the dead volume of the column, is collected by eluting with the same sodium chloride solution. A sufficient amount of 1M aqueous sodium bicarbonate solution is added to this fraction to obtain a final bicarbonate concentration of 0.1M, and 10 mg of histamine are then introduced. After 24 hours at 18° C., the solution is chromatographed on a column consisting of approximately 50 ml of Trisacryl GF05, equilibrated with 0.15M sodium chloride solution buffered to pH 7.4 with 0.01M potassium phosphate buffer; elution is carried out with this same solution. The immunogen thereby obtained contains an average 2.6 molecules of histamine per molecule of albumin.

(2) Immunization of the mice 4 injections, including the booster injection, of the immunogen are carried out on the animals, subcutaneously in the proportion of 100 µg of antigen in 200 µl of Freund's complete adjuvant for the first two injections at an interval of 14 days, and intravenously in the proportion of 50 µg of antigen in 200 µl of physiological saline for the following two injections, which are carried out on the same day and 4 days after the second.

The sacrifice of the animals and the isolation of the spleen cells takes place 3 days after the final injection.

(3) Fusion

The fusion with suitable SP 2/0 hybridoma cells is carried out in the presence of polyethylene glycol 1000, marketed by MERCK.

(4) Selection of the hybridomas

Culturing of the clones and subclones is performed in RPMI 1640 medium supplemented with 10% of horse serum; the composition of the conventional medium being mentioned in In Vitro 9, p. 6 (1974). The clones are selected by studying the content of the supernatents of the culture wells by the so-called ELISA (enzyme linked immunosorbent assay) method, that is to say "the assay method using an enzyme bound to an immunoabsorbent".

(5) Selection

From primary cultures, using the technique of analysis of the supernatants described above, 2 clones were thus isolated, the affinity of which for the histamine/p-benzoquinone/albumin conjugate is distinctly greater than that for free histamine.

For the reference clone D22-12, filed with the CNCM under the no. I-421, the relative affinities of the secreted monoclonal antibody are shown in Table 1.

TABLE 1

| Nature of the antigen | relative affinity |
| --- | --- |
| Histamine/p-benzoquinone/albumin conjugate | 1 |
| Free histamine | $0.5 \times 10^{-5}$ |
| p-Benzoquinone/albumin conjugate | $-\infty$ |
| Albumin alone | $-\infty$ |

EXAMPLE 2

"Direct" type determination of histamine (1) Preparation of immobilized p-benzoquinone 100 µl of a bovine albumin solution of concentration 10 µg/ml in phosphate-buffered saline (PBS) containing 0.02% weight per volume of sodium azide are introduced into each well of a polystyrene microtitration plate. The plate is covered and then incubated for 2 hours at 60° C. and overnight at 4° C. The liquid is removed from the wells which are then washed with sodium phosphate solution (0.1M; pH 4.5).

Into each of the wells treated in this manner, 100 µl of a para-benzoquinone solution of concentration 3 mg/ml in a 10% volume per volume of mixture of ethanol and potassium phosphate (0.1M; pH 4.5) are then introduced. The covered plate is maintained for 1 hour at 4° C. in the dark. The liquid is decanted and the wells are washed with phosphate buffer (0.1M; pH 4.5) to remove the excess benzoquinone.

(2) Binding of the histamine to be determined

The sample (control or test) is diluted with sodium bicarbonate buffer (0.1M) to obtain a pH of 8.5, so as to arrive at a histamine concentration of between 0.1 and 20 ng/ml.

100 µl of this dilution are than introduced into the wells of the plate which have been obtained as above and the covered plate is maintained for 4 hours at 37° C. The liquid is then removed from the wells and these are washed with a solution referred to as TBS, consisting of an aqueous soluton of TRIS (0.01M; pH 7.4) and NaCl (0.15M) into which a conventional surfactant, TWEEN 20, has been introduced in the proportion of 0.1%.

(3) Complexing

To obtain large amounts of monoclonal antibodies, a known method was applied: ascites formation in mice into which the monoclonal antibodies secreted by the preferred hybridoma cells, isolated in Example 1, are injected intraperitonally with hybridoma cells, and isolation of the ascites fluid. The monoclonal antibodies are diluted in TBS containing 1% of bovine albumin and 0.1% of TWEEN 20 to obtain solutions of concentration in the region of 1 µg/ml.

Into each of the wells treated above, 100 µl of dilution of monoclonal antibodies are introduced and the plate is left for 1 night at room temperature. The liquid is then removed from the wells and these are washed with TBS solution containing 0.1% of TWEEN 20.

(4) Visualization (a) Anti-(mouse IgG) antibodies labeled with β-galactosidase are diluted in TBS solution containing 0.02% weight per volume of sodium azide to obtain antibody concentrations of between 1 and 5 µg/ml. 100 µl of these solutions are introduced into each well and the covered plate is left for 2 hours at room temperature before the liquid is removed from the wells and the latter are washed with TBS containing 0.1% of TWEEN 20.

(b) 200 µl of a buffered aqueous solution of a specific substrate for β-galactosidase, ortho-nitrophenylgalactopyranoside, of concentration 0.8 mg/ml, is then introduced into each of the walls. After 2 to 4 hours at 37° C., the enzyme reaction is stopped by adding 50 µl of aqueous $Na_2CO_3$ solution (2M) and the amount of substrate converted is determined by reading the optical density of the solution present in the microwells. FIG. 1 shows, in semilogarithmic coordinates, the optical density at 414 nm read in terms of the histamine concentration, after dilution, in the starting sample, expressed as ng of histamine per ml.

It is found that, under these conditions, the threshold of detection of histamine is in the region of 20 pg/100 µl.

EXAMPLE 3

Determination of histamine by the enzymoimmunometric method (1) Reaction of the amine with p-benzoquinone The same to be determined, or the control sample, containing histamine is mixed (volume for volume) in small tubes with a solution of p-benzoquinone of concentration 6 mg/ml in phosphate buffer (0.1M; pH 4.5) containing 20% (V/V) of ethanol, to obtain a solution having a final volume of approximately 0.5 ml. The mixture is left at room temperature for 1 hour in the dark.

(2) Blocking of the reactive groups

50 µl of an aqueous solution of glycine (2M) and sodium carbonate (2M) are then introduced into each of the tubes to obtain a final pH of between 7.5 and 8.5 and the mixture is left at room temperature for 1 hour in the dark.

(3) Complexing

90 µl of a solution of monoclonal antibody, obtained above, in an aqueous monopotassium phosphate solution (0.5M) containing 10% (W/V) of bovine serum albumin and 0.1% of TWEEN 20, are then introduced such that the antibody concentration is in the region of 100 ng/ml.

The tubes are left at room temperature for 20 hours.

(4) Visualization

The solutions present in the tubes are then introduced into the microwells of a plate, on the walls of which histamine have been bound via bovine serum albumin, as described in Example 2-1 and 2-2, in the proportion of 1 µg of histamine per well.

Into each of the wells filled in this manner, a solution of labeled anti-mouse IgG antibodies is then added under the conditions described in Example 2 (4-a), and visualization is performed as in Example 2 (4-b).

Figure 2:
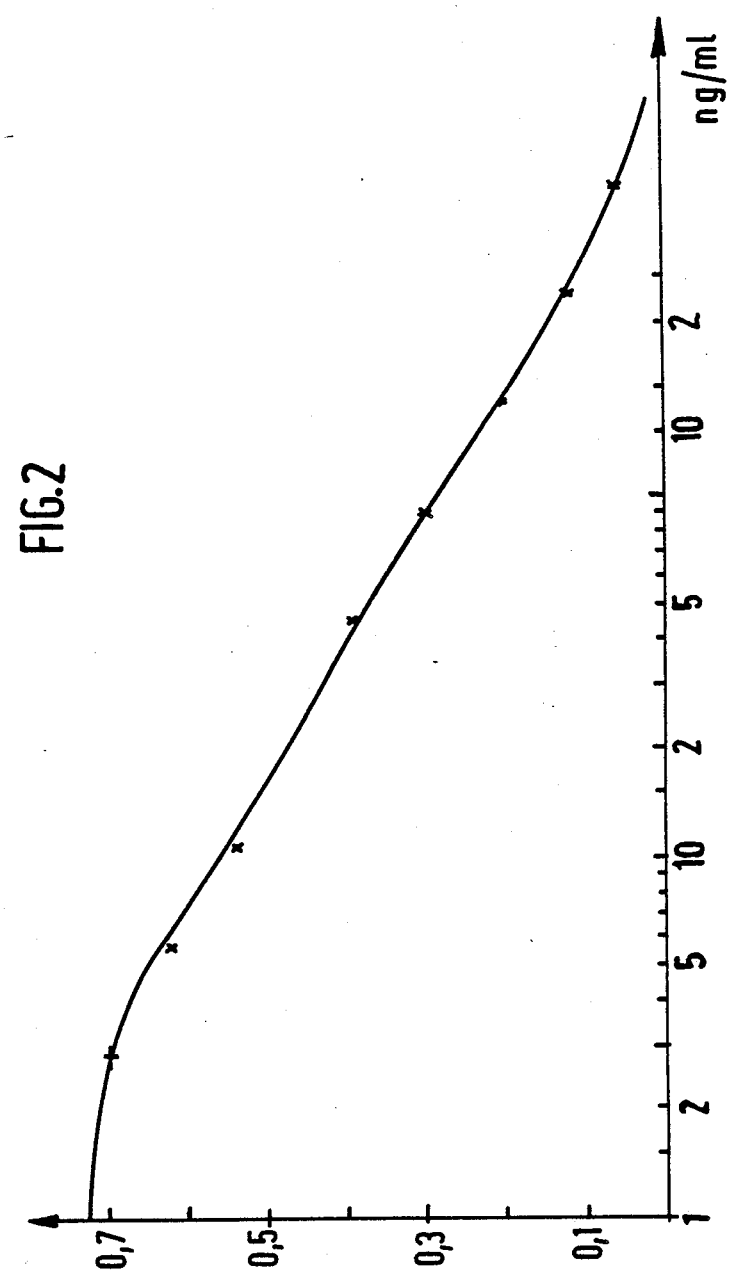
FIG. 2 shows optical density read in terms of histamine concentration.

The measured enzyme activity is almost inversely proportional to the histamine concentration in the starting sample, as can be seen in FIG. 2, in which there is plotted the optical density read in terms of the histamine concentration in the solution.

The detection threshold with the monoclonal antibodies secreted by the reference hybridomas D22-12 under these conditions is consequently 5 ng/ml.

EXAMPLE 4

Figure 3:
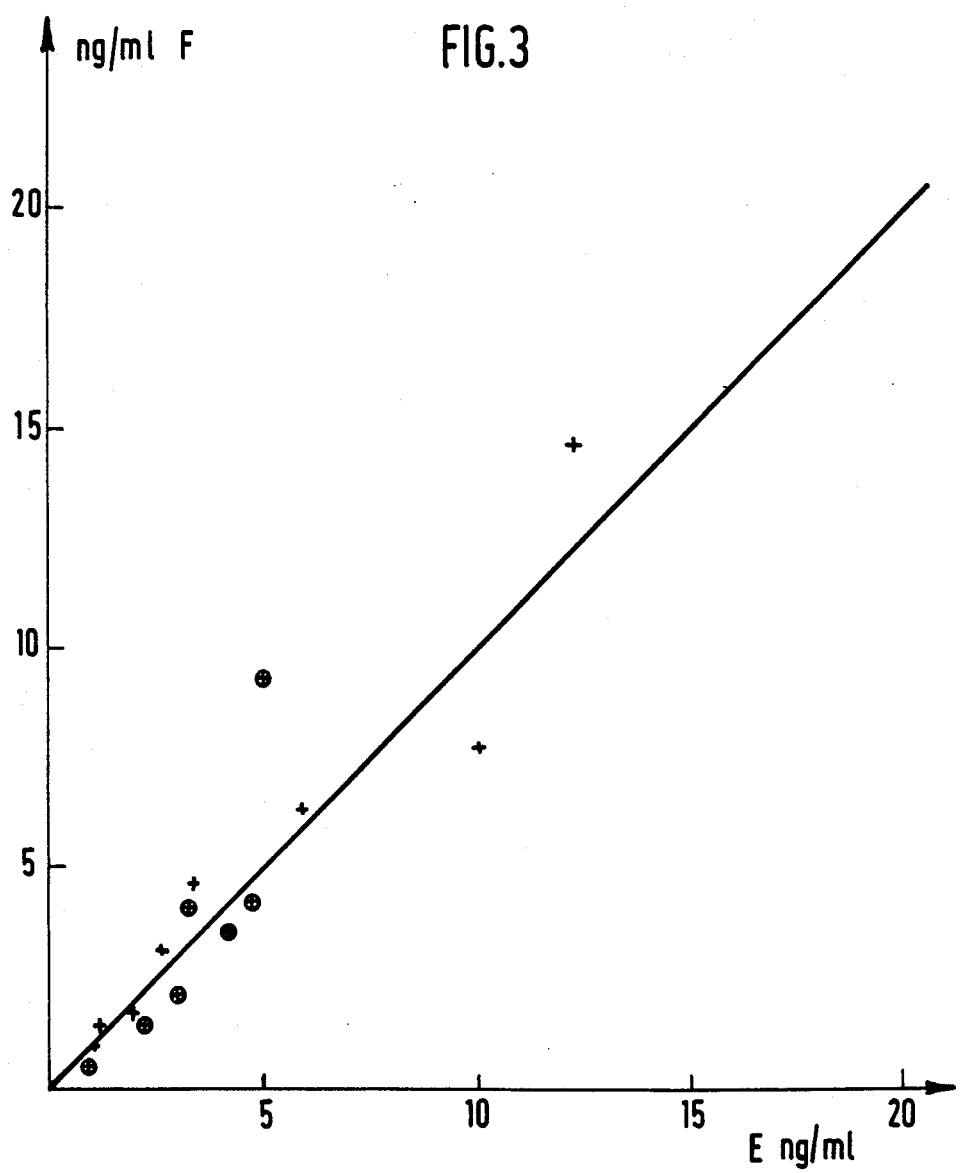
FIG. 3 shows a comparison between results obtained by the method of the invention and those obtained by a known fluorimetric method.

Comparison between the results obtained with the direct method according to the invention and a known fluorimetric method 22 samples of solutions containing histamine at various concentrations were determined successively by both methods. These solutions were obtained from lung washings of guinea-pigs sensitized with ovalbumin. In FIG. 3, the results obtained with the direct type method according to the invention (E) are plotted as abscissi and those obtained with the fluorimetric method (F) as ordinates; it is seen in this figure that there is positive correlation between the results obtained by the two methods. In this FIG. 3, the points "X" represent one series of experiments and the points " x " another series of experiments carried out one week later with different samples.

EXAMPLE 5

Preparation of the peroxidase-histamine reagent (a) 10 mg of horse-radish peroxidase are dissolved in 1.7 ml of 0.1M phosphate buffer pH 7.0. 0.3 ml of a solution containing 30 mg of 1,4-benzoquinone in 1 ml of ethanol is then added. The mixture is left to react in the dark for 1 hour at room temperature.

The peroxidase covalently linked to the 1,4-benzoquinone is separated from the unreacted benzoquinone by gel filtration (2.5×8 cm column of Trisacryl GF 05), followed by washing with 0.15M NaCl solution. The first brown fraction is collected and mixed with 0.5 ml of sodium borate/potassium phosphate buffer pH 9.0, according to Kolthoff (1932), containing 100 mg of histamine dihydrochloride. The pH is adjusted to 8.5 by adding one volume of saturated sodium borate buffer. The mixture is left at room temperature for 20 hours in the dark, and then dialyzed against cold TBS buffer for 24 hours.

(b) A variant of the above procedure (a) consisting in adding 0.01 ml of alcoholic solution of 1,4-benzoquinone [10 ml/ml] to a solution containing 0.1 mg of histamine dihydrochloride (dissolved in 0.1 ml of 0.1M potassium phosphate buffer at pH 4.5).

The mixture is left for 1 hour at room temperature in the dark. 0.5 ml of horse-radish peroxidase solution (10 mg dissolved in 0.5 ml of sodium borate/potassium phosphate buffer pH 9) is then added. The mixture is left over night at room temperature, is then passed through a chromatography column over Trisacryl GF 05, and the first brown fraction is collected.

EXAMPLE 6

Determination of histamine according to the invention, by the competition method (a) Reaction of histamine with benzoquinone The histamine-1,4-benzoquinone coupling has been described in Example 3 above.

After blocking of the reactive groups and neutralization according to Example 3, the complexing reaction is performed.

(b) Complexing and competition

The histamine is bound to the immobilized monoclonal antibodies according to the following procedure:

0.1 ml of a solution of histamine treated with benzoquinone is placed in each well of the microplate, on the walls of which the monoclonal antibodies according to the invention have been bound. The plate is incubated overnight at room temperature, and 0.1 ml of a solution of histamine-peroxidase conjugate, "TBS-TWEEN 20 (0.1% volume/volume)-BSA (1%)" buffer is then added.

After 2 hours' incubation at room temperature, the plate is washed three times with TBS-TWEEN 20 buffer (containing 0.1% of TWEEN 20 by volume).

Finally, the peroxidase activity associated with the solid phase of the microplate is measured by adding 0.2 ml of 0.05M citrate buffer containing 1 mg/ml of orthophenylenediamine and 0.06% of hydrogen peroxide.

After 10 minutes, the enzyme reaction is stopped by adding 0.05 ml of 2N sulfuric acid containing 0.5% of $Na_2SO_3$. The reading is taken at 492 nm.

Figure 4:
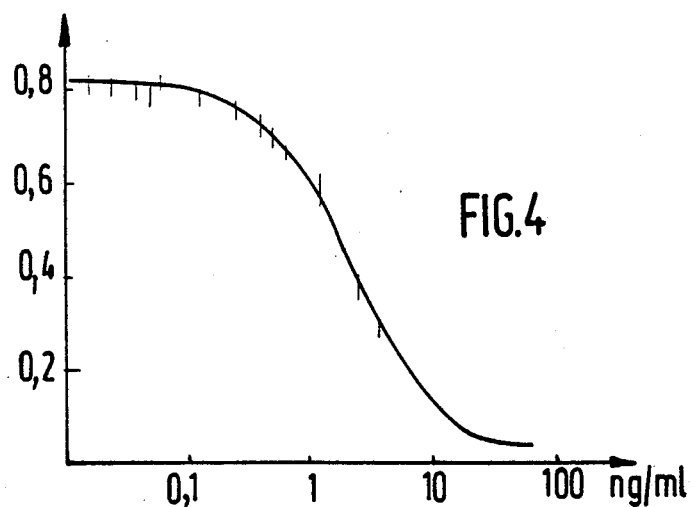
FIG. 4 shows, in semi-logarithmic co-ordinates, optical density at 492 nm read in terms of histamine concentration.

FIG. 4 shows, with semi-logarithmic coordinates, the optical density at 492 nm read in terms of the histamine concentration, after dilution, in the starting sample, expressed as ng of histamine per ml.

(c) Comparison between the results obtained by the competitive method and those obtained by a known fluorimetric method (determination of histamine from whole human blood)

Figure 5:
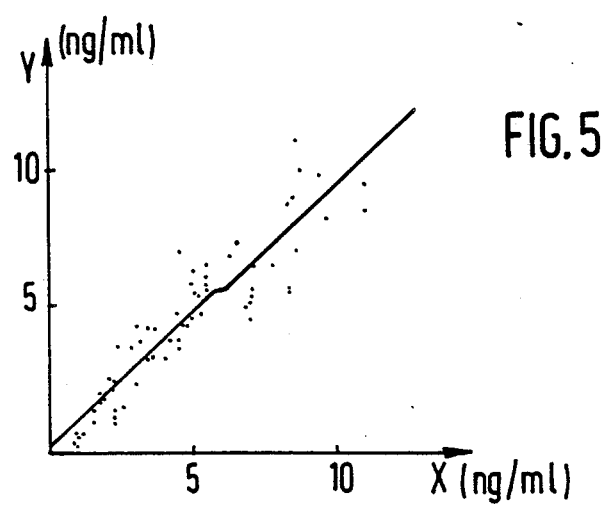
FIG. 5 shows a comparison between results obtained by the competitive method and those obtained by a known fluorimetric method.

In FIG. 5, the measurement carried out according to the competitive method (ELISA) is plotted on the ordinate (y) axis and the measurement obtained by fluorescence is plotted on the abscissa (x) axis. It is seen in this figure that there is positive correlation between the results obtained by the two methods.

We claim:

1. A method for immunological determination of amines in biological media, wherein:
   (a) the amine suspected of being present in the sample is reacted with a quinone;
   (b) a monoclonal antibody which specifically recognizes the amine-quinone reaction product formed is then introduced into the medium; and
   (c) determination is carried out for either a free or immobilized form of the monoclonal antibody present as an indication of the presence of an amine.

2. The method as claimed in claim 1 wherein, between stage (a) and stage (b), the remaining reactive groups of the quinone are blocked.

3. The method as claimed in claim 1 wherein, in stage (a), the quinone is used in the immobilized state on an insoluble support, the immobilization being achieved by the use of a polymer having amine groups, and wherein, in stage (c), determining the monoclonal antibody present in its complexed form with the amine-quinone reaction product is carried out.

4. The method as claimed in claim 1 wherein, in stage (a), the quinone is used in the free state, and wherein, in stage (c), the monoclonal antibody is determined in its free state.

5. The method as claimed in claim 4 wherein, in stage (c), a known amount of compound resulting from the reaction of the amine present in the same with the quinone, the latter being immobilized on an insoluble support by a polymer having amine groups, is introduced into the medium, together with an antibody directed against the monoclonal antibody and labeled with a measurable component, and, after the reaction, determining the amount of labeled antibody which has bound to the said support bearing the quinone-amine reaction product, wherein the amount of labeled antibody is an indication of the presence of an amine.

6. The method as claimed in claim 4 wherein, in stage (c), the monoclonal antibody is immobilized on a support, an enzyme-amine conjugate is added to the medium and the enzyme is then determined, either on the support or in the liquid phase.

7. The method as claimed in claim 7, wherein a peroxidase is used as the enzyme.

8. The method as claimed in claim 1, wherein the amine in the sample is a primary amine.

9. The method as claimed in claim 9, wherein the amine in the sample is histamine.

10. The method as claimed in claim 1 wherein, in stage (a), p-benzoquinone is used as the quinone.

11. The monoclonal antibodies specific for the product resulting from the reaction of a quinone with a primary or secondary amine.

12. The monoclonal antibodies as claimed in claim 12, which are specific for the product resulting from the reaction of a primary amine with p-benzoquinone.

13. The monoclonal antibodies as claimed in claim 11, which are specific for the compound resulting from the reaction of p-benzoquinone and histamine.

14. The monoclonal antibodies as claimed in claim 14, having the characteristics of those secreted by the hybridoma cell line which have been deposited with the CNCM under the no. I-421.

15. Hybridoma which secrete a monoclonal antibody as claimed in claim 11.

16. Hybridoma which secrete a monoclonal antibody as claimed in claim 12.

17. Hybridoma which secrete a monoclonal antigody as claimed in claim 13.

18. Hybridomas having the characteristics of those belonging to the cell line which have been deposited with the CNCM under the no. I-421.

19. A kit of reagents for the application of the method as defined in claim 1, which comprises separate containers separately containing:
- a quinone;
- a monoclonal antibody specific for the product resulting from the reaction of quinone with the amine to be determined; and
- a system for the determination of the monoclonal antibody.

20. A kit of reagents for the application of the method of claim 5, comprising separate containers separately containing:
- a free quinone;
- a monoclonal antibody specific for the product resulting from the reaction of quinone with the amine present in the sample; and
- a system for the determination of the monoclonal antibody, in which the system for determining the monoclonal antibody comprises a compound resulting from the reaction of the amine present in the sample and the quinone, the latter being immobilized on an insoluble support by a polymer having amine groups, together with a second antibody directed against the monoclonal antibody and labeled with a measurable component.

21. A kit of reagents for the application of the method of claim 6, comprising separate containers separately containing:
- a free quinone;
- a monoclonal antibody specific for the product resulting from the reaction of quinone with the amine present in the sample; and
- a system for the determination of the monoclonal antibody, comprising an enzyme-amine conjugate.

22. The kit of claim 19 further comprising a compound capable of blocking the reactive groups of the quinone.

23. The kit of claim 20 further comprising a compound capable of blocking the reactive groups of the quinone.

24. The kit of claim 21 further comprising a compound capable of blocking the reactive groups of the quinone.

* * * * *

UNITED STATES PATENT AND TRADEMARK OFFICE
CERTIFICATE OF CORRECTION

PATENT NO. : 4,900,661

DATED : Feb. 13, 1990

INVENTOR(S) : Jean-Luc Guesdon, et al

It is certified that error appears in the above-identified patent and that said Letters Patent is hereby corrected as shown below:

Column 10, line 44, claim 7, "claim 7" should read --claim 6--.
Column 10, line 61, claim 14, "claim 14" should read --claim 13--.

Signed and Sealed this

Third Day of March, 1992

Attest:

HARRY F. MANBECK, JR.

*Attesting Officer*  *Commissioner of Patents and Trademarks*